(12) United States Patent
Hirata et al.

(10) Patent No.: US 10,433,801 B2
(45) Date of Patent: Oct. 8, 2019

(54) X-RAY PHOTOGRAPHING DEVICE

(71) Applicant: SHIMADZU CORPORATION, Nakagyo-Ku, Kyoto-Shi, Kyoto (JP)

(72) Inventors: Goro Hirata, Kyoto (JP); Masahiro Kawano, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 112 days.

(21) Appl. No.: 15/574,400

(22) PCT Filed: May 18, 2016

(86) PCT No.: PCT/JP2016/064693
§ 371 (c)(1),
(2) Date: Nov. 15, 2017

(87) PCT Pub. No.: WO2016/186123
PCT Pub. Date: Nov. 24, 2016

(65) Prior Publication Data
US 2018/0132809 A1 May 17, 2018

(30) Foreign Application Priority Data
May 21, 2015 (JP) ................................. 2015-002498

(51) Int. Cl.
*A61B 6/00* (2006.01)
(52) U.S. Cl.
CPC .................................... *A61B 6/447* (2013.01)
(58) Field of Classification Search
None
See application file for complete search history.

(56) References Cited

U.S. PATENT DOCUMENTS 6,363,704 B2 * 4/2002 Kim ..................... D07B 1/0686
57/211

FOREIGN PATENT DOCUMENTS

JP   3-55033    3/1991
JP   6-327660   11/1994

OTHER PUBLICATIONS

PCT/JP2016/064693, International Search Report and Written Opinion dated Aug. 9, 206, 2 pages—English, 6 pages—Japanese.
Microfilm of the specification and drawings annexed to the request of Japanese Utility Model Appln. No. 12092071974 (Laid-open No. 47668/1976), (Tokyo Shihaura Electric Co., Ltd.), Apr. 8, 1976, pp. 4-6; 1 page—English, 2 pages—Japanese.

* cited by examiner

*Primary Examiner* — Hoon K Song
(74) *Attorney, Agent, or Firm* — Andrew F. Young, Esq.; Lackenbach Siegel, LLP

(57) ABSTRACT

The purpose of the present invention is to prevent the risk when the wire-rope that is hanging an X-ray irradiation element including an X-ray tube breaks.
The X-ray imaging apparatus to solve the above problem comprises a wire-ropes 17, 18 that hang and support an X-ray irradiation element 5 and have a different fatigue strength each other, wherein the different between the fatigue progressions of the wire-ropes 17, 18 takes place, the wire-rope 17 or the wire-rope 18 having a weaker fatigue strength breaks first and both wire-ropes 17, 18 never break simultaneously.

2 Claims, 3 Drawing Sheets

X-RAY PHOTOGRAPHING DEVICE

CROSS REFERENCE TO RELATED APPLICATIONS

This application relates to and claims priority as a § 371 from Ser. No.:PCT/JP2016/064693 filed May. 18.2016, the entire contents of which are incorporated herein by reference, and which in turn claims priority from JP Ser. No.: 2015-002498 filed May. 21, 2015.

TECHNICAL FIELD

The present invention relates to an X-ray imaging (photographing) apparatus (device) that comprises an X-ray irradiation element, including an x-ray tube, that is hanged with a wire-rope.

BACKGROUND

A common medical X-ray imaging apparatus includes; an overhead traveling system, in which an X-ray irradiation element, including an X-ray tube, is supported liftably (movable up-and-down) along the supporting post installed downward from a carriage, which is movable on the rail installed on the ceiling; a fixed system, in which the X-ray irradiation element, including an X-ray tube, is supported liftably along the supporting post installed on the floor nearby the table on which a subject is lying; and a round (movable) system, in which the X-ray irradiation element, including an X-ray tube, is supported liftably along the supporting post being hanged from the movable platform. Normally, the X-ray irradiation element, including an X-ray tube, is being hanged with at least two wire-ropes inside the supporting post in any X-ray imaging apparatus.

The X-ray irradiation element, including an X-ray tube, can be hanged with one wire-rope, but in such case, the diameter thereof must be essentially large due to a fatigue strength design-wise, and consequently, flexibility is lost due to such large diameter of the wire-rope, so that at least two flexible wire-ropes having an adequate diameter are commonly used due to restriction of a pulley and an apparatus size.

In such X-ray imaging apparatus, a breaking wire detection mechanism that detects breaking of the wire-rope is equipped to prevent a falling-down incident of the X-ray irradiation element, including an X-ray tube due to breaking of the wire-rope. For example, relative to the overhead traveling system X-ray Imaging apparatus, the X-ray tube thereof is being hanged with a plurality of wire-ropes and the breaking of the wire-ropes is always monitored by the breaking detection mechanism and when the breaking detection mechanism detects breaking of the wire-rope, the breaking mechanism locks the lifting of the X-ray irradiation element, including an X-ray tube (refer to the Patent Document 1).

RELATED PRIOR ART DOCUMENTS

Patent Document

Patent Document 1: JP Patent Published 2008-183109

SUMMARY OF THE INVENTION

Objects to be Solved

According to the aspect of the conventional X-ray imaging apparatus, the X-ray irradiation element, including an X-ray tube, are being hanged with at least two wire-ropes, and commonly, the weight is equally loaded to at least two wire-ropes having the same fatigue strength, so that a material fatigue of the wire-ropes takes place along the change of the wire-ropes with time progresses equally relative to each wire-rope. Therefore, in the worst scenario, both wire-ropes may break simultaneously.

In such scenario, lifting of the X-ray irradiation element, including the X-ray tube, cannot be locked by the breaking mechanism, so that a risk, on which the X-ray irradiation element falls down, becomes accountable.

The purpose of the present invention is to solve the problem of the conventional technology and is to provide an X-ray imaging apparatus in which at least two wire-ropes hanging an X-ray irradiation element, including an X-ray tube, never break simultaneously.

Means for Solving the Problem

An X-ray imaging apparatus of the present invention according to the claim 1 is the X-ray imaging apparatus, in which at least two wire-ropes are hanging and lifting an X-ray irradiation element, including an X-ray tube, to solve the problem as set forth above, and at least two wire-ropes comprises each of the wire-ropes having a different fatigue strength one another.

The fatigue strength is the maximum of stress amplitude at which the material never breaks even if infinite stresses are added when a stress is added repeatedly to the material and can be obtained by a fatigue test.

In addition, an X-ray imaging apparatus of the present invention according to the claim 2 is the X-ray imaging apparatus according to the claim 1, in which the other end of wire-rope connected to the X-ray irradiation element is connected to a balancing mechanism that balances out the total weight of the X-ray irradiation element via a pulley.

A counter weight or a spring bias (force) mechanism is applied to the balancing mechanism.

In addition, an X-ray imaging apparatus of the present invention according to the claim 3 is the X-ray imaging apparatus according to the claim 1 or the claim 2, comprises a means that detects breaking of a wire-rope having smaller (weaker) fatigue strength.

A variety of detection means that detects breaking of the wire-rope is available, but a mechanical micro-switch that detects tension of the wire-rope is preferable.

Effect of the Invention

According to the aspect of the present invention, at least two wire-ropes comprises each of the wire-ropes, hanging the X-ray irradiation element, including an X-ray tube, that has the different fatigue strength one another, so that the progressive fatigue level of the wire-ropes is different each other and the wire-rope having a weaker fatigue strength breaks always first and all wire-ropes, at least two wire-ropes, never break simultaneously.

Therefore, the breaking detection means detects arbitrarily the broken wire-rope followed by replacing such wire-rope, so that a falling-down incident of the X-ray irradiation element, including an X-ray tube, can be obviated and consequently, the secure use can be continuously provided. In addition, when replacement is conducted, all wire-ropes including the unbroken wire-rope must be replaced at the same time.

DETAILED DESCRIPTION OF THE PREFERRED EMBODIMENTS

Next, referring to the FIGs., the inventor sets forth one example of the X-ray imaging apparatus according to the aspect of the Embodiment.

Figure 1:
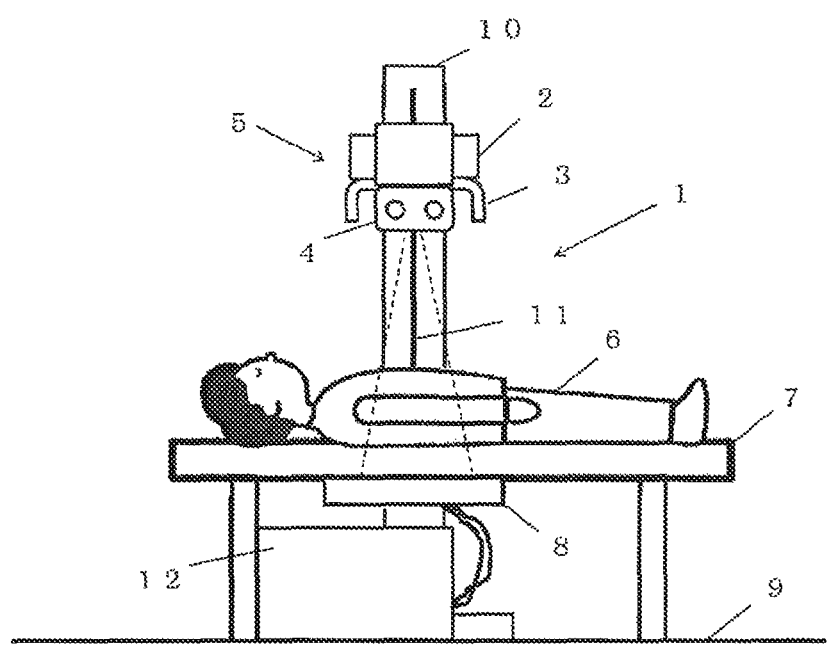
FIG. 1 is a schematic view illustrating the total system of the fixed-type X-ray imaging apparatus of the present invention.

FIG. 1 is a schematic view illustrating the total system of the fixed-type X-ray imaging apparatus of the present invention. Referring to FIG. 1, the X-ray imaging apparatus 1 comprises an X-ray irradiation element 5 further comprising an X-ray tube 2, a collimator (not shown in FIG.), an operation panel 3 and an operation handle 4. The X-ray irradiation element 5 is liftable along a guide slit (rail) 11 of the supporting post 10 installed on the floor surface 9 nearby the table 7 on which the subject 6 is lying and, as set forth later, is being hanged with two wire-ropes 17, 18 to be supported (refer to FIG. 2).

In addition, the flat panel detector 8 is installed to the backside of the table 7 facing the X-ray irradiation element 5 and also a housing 12 housing an X-ray high-voltage unit, an image processing device and an image control device in the low-side space of the table 7.

An X-ray irradiation area of X-rays irradiated from the X-ray tube 2 is specified by the collimator (not shown in FIG.) and the X-ray that transmits the subject 6 is detected by the flat panel detector 8. The detection value detected by the flat panel detector 8 is input into the image processing device, not shown in FIG., inside the housing 12, in which the image signal is stored and also the image signal is sent to the image display element following image processing, and the image display element displays the X-ray radiograph corresponding to the image signal.

Figure 2:
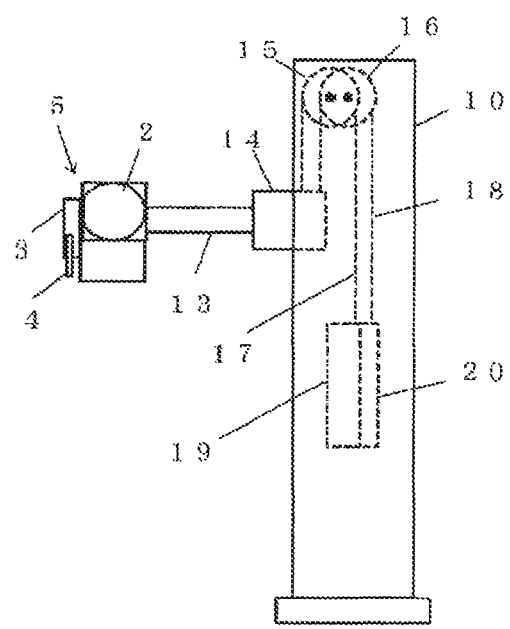
FIG. 2 is a schematic view illustrating the main system of the X-ray imaging apparatus of the present invention.

FIG. 2 is a schematic view illustrating the main system of the X-ray imaging apparatus of the present invention. The X-ray irradiation element 5, including the X-ray tube 2, the collimator (not shown in FIG.), the operation panel 3 and the operation handle 4, is held by a mounting block 14 via the support member 13.

The mounting block 14 connecting the one end of the wire-ropes 17, 18 winding the pulleys 15, 16 inside the support post 10 is being hanged. The other end of the wire-ropes 17, 18 connects the counter weights 19, 20 that balance out with the total weight of the supporting member 13, the mounting block 14 and the X-ray irradiation element 5. Such structure facilitates to lift the X-ray irradiation element 5 along the guide slit 11 (refer to FIG. 1) of the support post 10 by operating the operation handle 4.

In addition, instead of the counter weights 19, 20, the spring bias (force) can be applied to balance out.

The wire-ropes 17, 18 used in the X-ray imaging apparatus of the present invention used have a different fatigue strength from each other. Therefore, a difference between progressions of the fatigue of the wire-ropes 17, 18 takes place and either one of the wire-ropes 17, 18, which has a weaker-fatigue strength, breaks first always, so that at least both wire-ropes 17, 18 never breaks simultaneously. The suitable level of difference between the fatigue strengths can be experimentally obtained.

Figure 3:
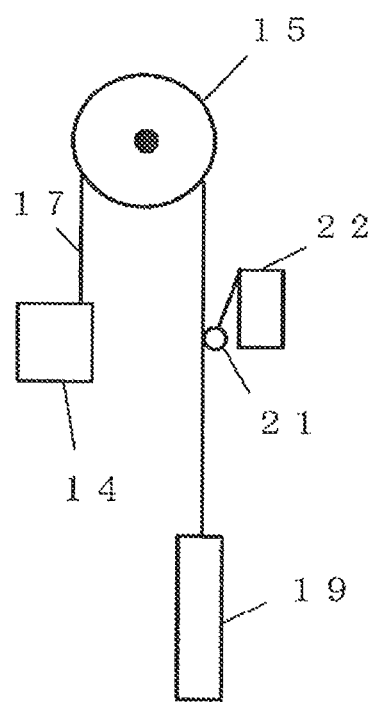
FIG. 3 is a schematic view illustrating an example of a breaking detection means of the wire-rope of the X-ray imaging apparatus of the present invention.

Breaking of the wire-ropes 17, 18 can be easily detected by an adequate breaking detection means. Referring to FIG. 3, the inventor sets forth such example. For example, the mechanical micro-switch 22 having the terminal 21 contacting the wire-rope 17, of which a fatigue strength is weaker, with a predetermined bias force can be applied thereto. The wire-rope 17 hangs the mounting block 14 and the counter weight 19 at both end through the pulley 15 and has consistently the constant tension, but once breaking takes place, the tension becomes almost free, so that the contacting terminal 21, which has been always on, turns off and consequently, breaking can be detected.

In general, it is satisfactory by detecting the breaking of the wire-rope 17, in the side of which the fatigue strength is weaker and which breaks first, but the same breaking detection means, e.g., such as the mechanical micro-switch 22, can be installed to the side of the wire-rope 18 to increase safety.

REFERENCE OF SIGNS

1 X-ray imaging apparatus
2 X-ray tube
3 Operation panel
4 Operation handle
5 X-ray irradiation element
6 Subject
7 Table
8 Flat panel detector
9 Floor surface
10 Supporting post
11 Guide slit
12 Housing
13 Supporting member
14 Mounting block
15, 16 Pulley
17, 18 Wire-rope
19, 20 Counter weight
21 Terminal
22 Mechanical micro-switch

What is claimed is:

1. An X-ray imaging apparatus, comprising:
   at least two wire-ropes selected from a group consisting of a plurality of wire-ropes each having a different fatigue strength, wherein:
   said at least two wire-ropes hang and lift an X-ray irradiation element including an X-ray tube;
   a pulley; and
   a balancing mechanism, wherein:
   each said wire-rope has a first end and a second end; and
   each said first end of each said wire-rope is connected to said X-ray irradiation element and each said second end thereof is connected to said balancing mechanism that balances out a total weight of said X-ray irradiation element through said pulley.

2. The X-ray imaging apparatus to claim 1, further comprising:
   a detection means that detects breaking of a wire-rope having a weaker fatigue strength among said wire-ropes.

\* \* \* \* \*